United States Patent
Heinold et al.

(10) Patent No.: US 6,298,506 B1
(45) Date of Patent: Oct. 9, 2001

(54) UROLOGICAL PATIENT BED

(75) Inventors: Michael Heinold, Oehringen; Friedrich K. Geist, Herzogenaurach, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/532,074

(22) Filed: Mar. 21, 2000

(30) Foreign Application Priority Data

Apr. 8, 1999 (DE) ................................. 199 15 852

(51) Int. Cl.[7] .................................................. A61G 13/12
(52) U.S. Cl. ................................. 5/613; 5/601; 378/209
(58) Field of Search .......................... 5/601, 613, 611, 5/86.1, 509.1; 378/209

(56) References Cited

U.S. PATENT DOCUMENTS

| | | | |
|---|---|---|---|
| 1,040,795 | * 10/1912 | Skeffington | ................................. 5/613 |
| 2,614,267 | * 10/1952 | Perri | ....................................... 5/86.1 |
| 2,872,259 | * 2/1959 | Thorpe | ....................................... 5/613 |
| 3,065,344 | * 11/1962 | Chervanka | ............................. 378/209 |
| 3,428,307 | * 2/1969 | Hunter et al. | ............................. 5/613 |
| 3,751,028 | 8/1973 | Scheininger et al. . | |
| 5,072,721 | 12/1991 | Weiler et al. . | |
| 5,184,363 | * 2/1993 | Falbo, Sr. | ................................. 5/613 |
| 5,754,997 | * 5/1998 | Lussi et al. | .............................. 5/601 |
| 5,919,131 | * 7/1999 | Smoler et al. | ............................ 5/613 |

FOREIGN PATENT DOCUMENTS 2 067 395   7/1981   (GB) .

* cited by examiner

*Primary Examiner*—Michael F. Trettel
(74) *Attorney, Agent, or Firm*—Schiff Hardin & Waite

(57) ABSTRACT

A urological patient bed has a table top supported by a pedestal, the table top being composed of a first plate section made of X-ray-transparent material and a second plate section, the first plate section and the second plate section being fashioned as separate plate modules that are adjacently arranged. These plate sections are detachably fastened so as to be exchangeable in their arrangement, so that different table top configurations can be selectively formed.

17 Claims, 3 Drawing Sheets

UROLOGICAL PATIENT BED

BACKGROUND OF THE INVENTION

1. Field of the Invention

The present invention is directed to a urological patient bed, of the type having a table top that is supported by a pedestal and that is comprised of a first plate section, made of X-ray-transparent material, and a second plate section.

2. Description of the Prior Art

Urological patient beds of the type above are known and serve for accepting a patient in order to examine him or her and if necessary to administer treatment. In the examination procedure, an X-ray image of the relevant body area of the patient is normally obtained, for which purpose this body area is arranged on the first plate section made of X-ray-transparent material. For example, the renal area is imaged in order to examine whether kidney stones are present. An X-ray device is appropriately positioned for that purpose. Subsequent to the pickup of the X-ray image and the corresponding evaluation, it may be necessary to move the patient to another bed for treatment with, for example, a lithotripsy device for the destruction of the kidney stones.

The arrangement of an urological patient bed in the examination room, in most cases, is such that the head end of the patient bed, namely the area in which the head of the patient lies, points toward the door. This arrangement is not always possible, however, due to spatial limitations imposed by the examination devices or treatment devices that are to be arranged at the side of the patient bed.

U.S. Pat. No. 3,751,028 discloses a patient bed having a pedestal with a guiding part at which a first plate section is arranged so as to be horizontally displaceable. Frame sections are provided at each of the left side and the right side of the first plate section. One frame section has a central frame part, at which another plate section is displaceably arranged. The other frame section is formed by two frame parts that are opposite to one another; a further plate section is also displaceably supported at these frame parts. Further, a head part is fastened at the frame sections.

German OS 39 15 381 discloses a bed for a lithotripter having a central segment that is rigidly fastened at the lithotripter; extending segments can be attached to this central segment on both sides and further segments can be attached to these extenders. A treatment window, which can be closed with an inset, is provided at the central segment; the therapeutic head of the lithotripter can be introduced into this treatment window.

German OS 31 01 373 describes an operating table having a table top with pivotable extension sections that can be attached to a central table section.

SUMMARY OF THE INVENTION

An object of the present invention is to provide a versatile patient bed.

This object is achieved in a urological patient bed of the above type having a first plate section and a second plate section fashioned as separate plate modules that are adjacently arranged, or that can be adjacently arranged, these plate modules being detachable and are exchangeably (detachably) fastened, or can be exchangeably fastened at the pedestal.

A particular advantage of the inventive patient bed is that a rigidly fastened table top or a rigidly fastened first plate section and second plate section are not utilized. Instead, these are modularly fashioned and can be arranged to one another in different positions, since they can be detachably and exchangeably fastened or attached at the pedestal holding device. It is thus possible to adapt the construction of the patient bed, in the framework of the installation, to the existing spatial requirements, so that the table layout can be arbitrarily selected facing right or left. It is thus advantageously possible to always orient the head end in the direction of the door, since the patient bed can be correspondingly reconfigured.

Moreover, the modular, variable construction of the inventive patient bed makes it possible for the treating physician to freely select the device side, namely the side from which the devices of the patient bed are approached or at which the devices are arranged. The inventive patient bed achieves an extremely flexible system and a system that is highly variable in its utilization.

In a further embodiment, additional extending plate sections can be arranged at one of the plate sections or at both plate sections. The further plate sections can also be fashioned in a modular manner and can be detachably arranged at the first plate section and/or the second plate section. In this embodiment of the invention, the table top is therefore composed of three modular pate sections, or (maximally) four modular plate sections, which are all detachable and which can be exchangeably attached. A highest degree of flexibility is thus achieved. A simple fastening of the plate section or of the further plate sections can be provided in the form of an insertion-type connection or insertion-type latch connection. Further, it has been proven advantageous when the two further plate sections have different lengths.

In order to enable an improved access possibility to the patient for a treatment device, particularly for the treatment head of a lithotripsy device, in a further embodiment a recess is provided at the second plate section, this recess being open toward one section side and which can be closed by means of a recess section that can be detachably inserted into the recess. The inventively provided recess at the second plate section, on which the treatment ensues by means of a lithotripsy device, for example, makes it possible to laterally introduce, in a simple way, the treatment head of the lithotripsy device into the recess or to bring it near the patient from below. When recess is closed the recess section, the full support surface is available when a treatment does not ensue. The recess should extend via at least one quarter of the width of the plate section. The recess should be dimensioned relatively small for patient comfort. Among other things, its size is also dependent on the size of the medical device to be introduced into the recess.

According to the invention, roller elements and/or support elements, which are arranged at the underside of the pedestal, can be mounted in a detachable manner and in a mirror-symmetric arrangement in order to provide sufficient stability for the patient bed in every configuration. Due to the selective arrangement of at least the first plate section and the second plate section and, as warranted, also the further plate sections, the center of gravity of the patient bed itself changes depending on the configuration as well as depending on different patients. In order to avoid an unintentional tilting, the inventively provided roller elements and/or support elements can be attached to the pedestal in a correspondingly mirror-symmetric manner, which means that the arrangement of these elements is dependent on the selected arrangement of the plate sections, so that a highest degree of stability is always produced. The roller elements can inventively include two fixed rollers and two guiding rollers and the support elements can inventively be a lifting mechanism with two lifter feet that can be placed on the bottom. The pedestal, together with the guiding rollers, is lifted at one end when the lifting mechanism is operated, so that it rests on the fixed rollers situated at one end of the pedestal and on the lifter feet situated at the other end of the pedestal. According to this inventive embodiment, the patient bed can be initially moved and positioned on the fixed rollers and the guiding rollers, whereupon the lifting mechanism is operated. Thereby, the guiding rollers are lifted; the pedestal then merely rests on the fixed rollers and the lifter feet and is advantageously sufficiently stabilized.

In order to be able to adjust any floor unevenness which may exist, so that a slight tilting, which can occur when a fixed roller or a lifter foot does not stand on the floor given a four-point-support, can be avoided, one lifter foot can be inventively fashioned as a spring-biased leveling foot, which is pressed onto the floor by spring force. Further, an immobilizing device can be inventively provided for the leveling foot for the purpose of immobilizing it after a final position has been reached. This immobilizing device can inventively include a pressure pin that can be guided through an opening in a guide bushing of the leveling foot and which, in the introduced position, exerts pressure on a brake lining that is arranged at the side of the bushing, so that the brake lining is pressed onto the shank of the leveling foot and thus immobilizes it.

In order to enable simple operation of the lifting mechanism, it can have a common driving arrangement for both lifter feet. The common driving arrangement can have a driving shaft, at which two cam disks are provided, which respectively engage lifters or pegs that are interactively connected to the respective lifter feet. In this embodiment, the movement of the lifter feet is controlled by the two identically fashioned cam disks.

In order to enable, apart from the lowering of the lifter feet, an automatic immobilization of the leveling feet when the lifting mechanism is operated, a second cam disk can be inventively allocated to the aforementioned cam disk allocated to the leveling foot; the pressure pin, or a guide pin that cooperates with this pressure pin, can be operated via the second cam disk. The first cam disk and the second cam disk are fashioned and/or arranged such that the pressure pin is not operated before the movement of the leveling foot effected by the first cam disk has been completed. When the lifting mechanism is operated, the lifter foot and the leveling foot, which are controlled via the first cam disk, are initially deployed at the same time. After a further movement of the driving shaft, at which the second cam disk is also arranged, the pressure pin, or a guide pin via which the pressure pin can be operated, are operated by this second cam disk, so that the pressure pin is then pressed onto the brake lining. The first cam disks, which are also moved due to the common arrangement on the driving shaft, no longer alter the position of the dies.

DESCRIPTION OF THE PREFERRED EMBODIMENTS

Figure 1:
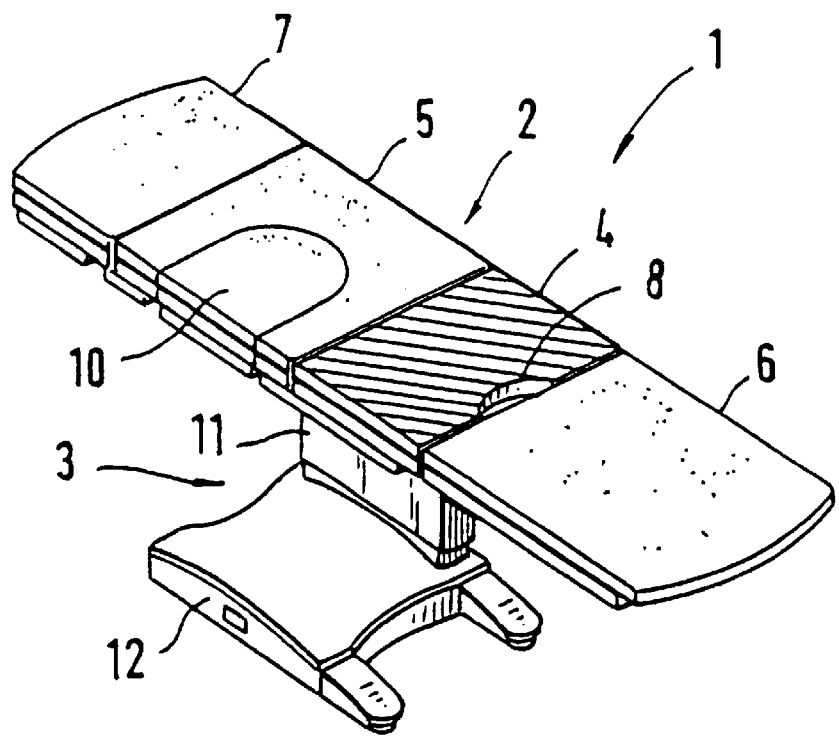
FIG. 1 is a perspective view of an inventive patient bed in a first configuration of the table top.

FIG. 1 shows an inventive urological patient bed 1, which is composed of a table top 2 that is supported by a pedestal 3. The table top 2 is composed of a first plate section 4 made of X-ray-transparent material, a second plate section 5 and further extending plate sections 6, 7 situated at the first plate section 4 or at the second plate section 5.

The first plate section 4 forms the examination area. The patient is arranged with the body area to be irradiated, the renal area, for example, on the first plate section. In the embodiment shown in FIG. 1, the head points in the direction of the further plate section 7. Further, a recess 8 is provided at the first plate section 4 at the perineal end allowing the physician to bring an examination instrument, for example, an endoscope, through the recess 8 near the patient from below, or the physician can bring the instrument near the patient from the side, given a detached further plate section 6.

The second plate section 5 forms the treatment area of the patient bed 1 that is to be used in the framework of a lithotripsy, for example. For example, after a kidney stone is conducted with an X-ray pickup, at the first plate section 4, the patient is placed with the renal area on the second plate section 5, where the destruction of the kidney stones ensues by means of a lithotripsy device (not shown). A recess 9 (see FIG. 2) is provided at the second plate section 5, which recess 9 can be selectively closed by means of a correspondingly dimensioned recess section 10 (see FIG. 1), so that the physician can approach the patient, in a simple way, with the lithotripsy device, or the treatment head thereof. For example, when the patient lying on his or her back is to be approached with the treatment head from below, the recess section 10 is removed, so that the patient partially lies over the recess 9. A device side of the patient bed is defined by means of this recess 10, since X-ray devices or lithotripsy devices are always to be applied from this side.

Figure 2:
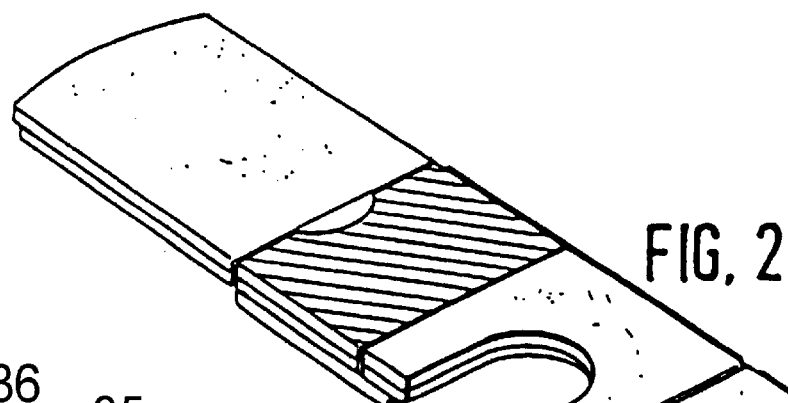
FIG. 2 is a perspective view of the patient bed of FIG. 1 with a modified table top configuration.

The two plate sections 4, 5 are modularly fashioned and are detachably arranged with respect to the pedestal 3. This means that they can be exchanged in their position to one another, if required (as shown in the FIGS. 1 and 2). In FIG. 1, the first plate section 4 is situated on the right side of the second plate section 5; FIG. 2 shows the reversed configuration. As a result, the head end of the patient bed 1 can be selectively oriented toward the right side or the left side.

Figure 7:
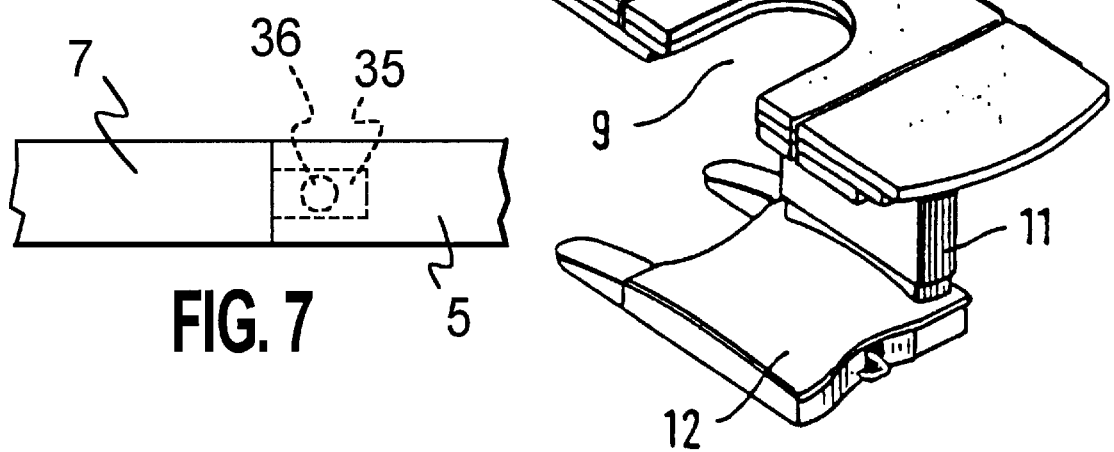
FIG. 7 is a side view of a portion of the inventive patient bed showing attachment of one of the further extending plate sections.

The further plate sections 6, 7, which are attached to the respective plate sections 4, 5, for example, by means of an insertion-type connection 35 or insertion-type latch connection 36 (FIG. 7), and are also modularly fashioned. They can also be exchanged with one another, which means that the plate section 6 can also be attached to the second plate section 5. For example, this is the case when the right kidney is initially treated in the framework of the lithotripsy and when the patient is subsequently turned around for purposes of treating the left kidney; this means that the head then lies on the other side. In order to offer a sufficient support surface for the entire body, the longer plate section 6 is correspondingly attached to the other side.

As can be seen from the FIGS. 1 and 2, the pedestal is formed by a vertical pedestal section 11 and a pedestal base 12. A number of roller elements and support elements are provided at the pedestal bottom (see FIG. 3), which is also variable with respect to the changes of the center of gravity caused by the variability of the table top construction. This means that the arrangement of the roller elements and support elements is selected depending on the selected table top configuration.

Figure 3:
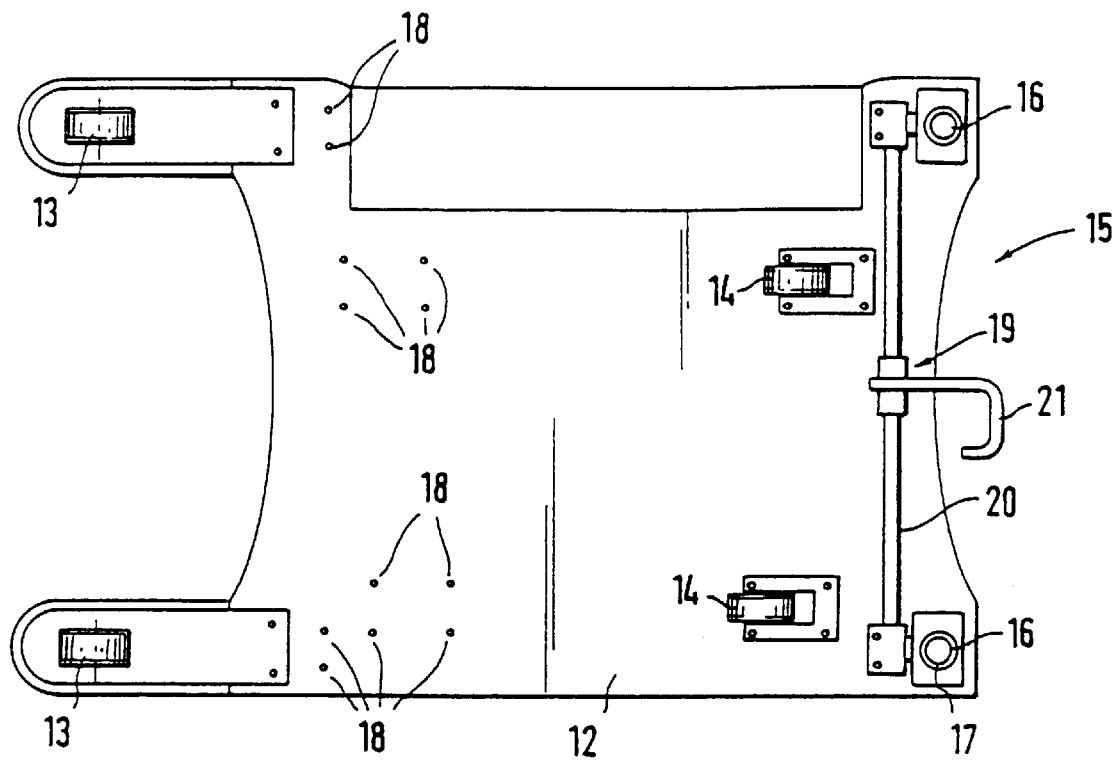
FIG. 3 is a bottom view of the pedestal of the inventive patient bed.

As can be seen from FIG. 3, the roller elements include two fixed rollers 13 and two guiding rollers 14; the support elements include a lifting mechanism 15 that has two lifter feet 16. One of the lifter feet 16 is fashioned as a leveling foot 17. Corresponding fastening bores 18 are provided at the pedestal bottom 12 in a mirror-symmetric arrangement. These fastening bores enable the attachment, in a mirror-symmetric manner with respect to the arrangement shown in FIG. 3, of the fixed rollers 13, the guiding rollers 14 and the entire lifting mechanism 15.

Figure 4:
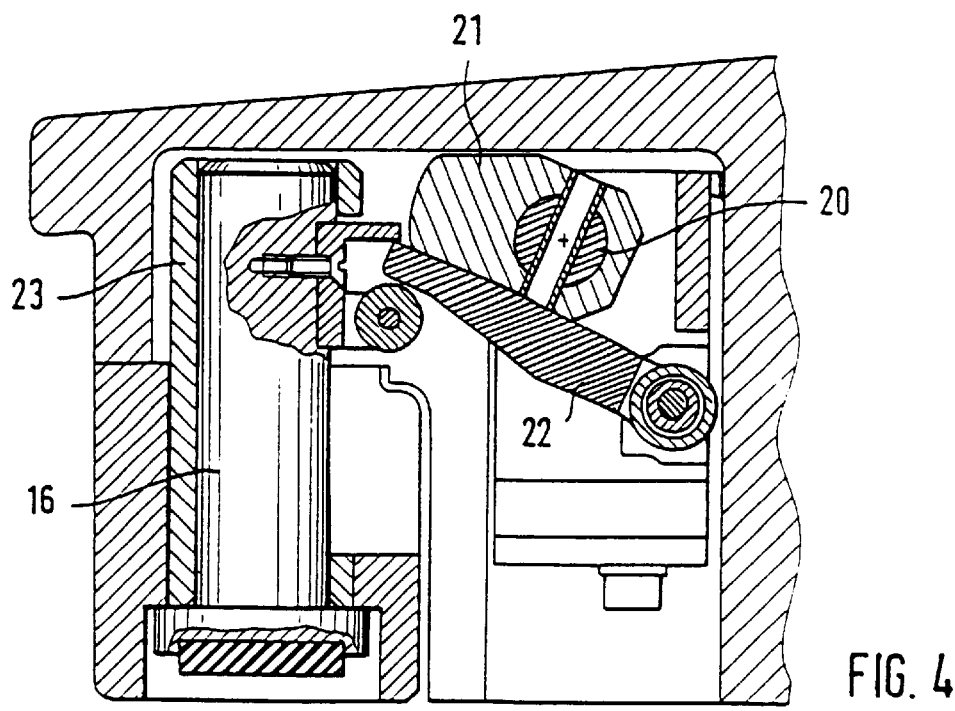
FIG. 4 is a sectional view through a part of the lifting mechanism with a lifter foot situated at a side of the pedestal.
Figure 5:
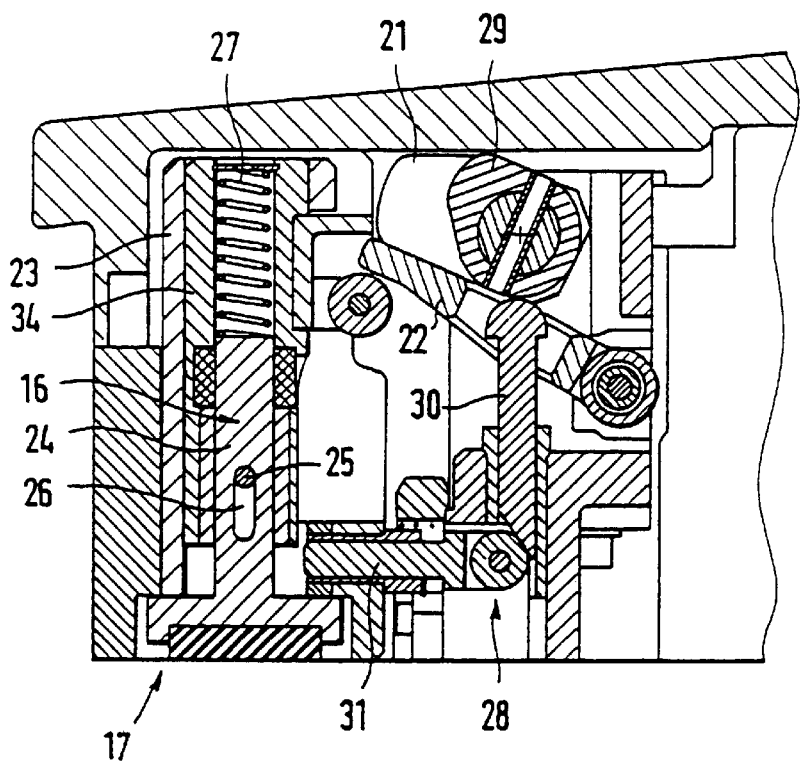
FIG. 5 is a sectional view through the part of the lifting mechanism with a leveling foot in the non-deployed position situated at the other side of the pedestal.
Figure 6:
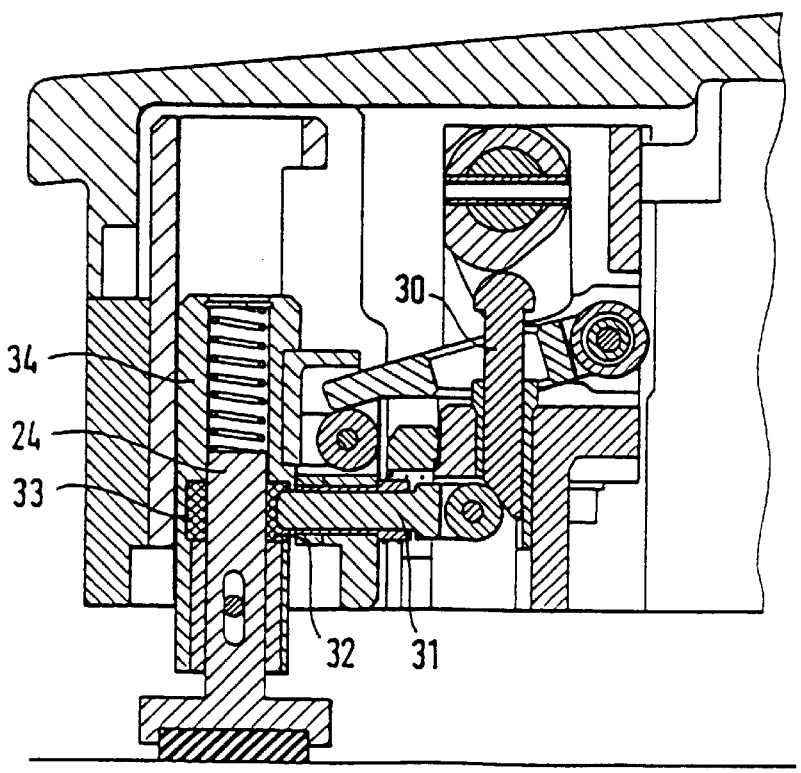
FIG. 6 shows the leveling foot from FIG. 5 in the deployed position.

For positioning the patient bed, it initially rests on the fixed rollers 13 and the guiding rollers 14. For immobilization after the final position has been reached, the patient bed is put on the two fixed rollers 13 and on the two lifter feet 16 by operating the lifting mechanism. The two guiding rollers 14 are thereby lifted from the floor. The lifting mechanism 15 has a common driving element 19 for both lifter feet 16 with a common driving shaft 20, which can be pivoted via an operating element 35 that can be activated by foot. As can be seen from the FIGS. 4 and 5, the transfer of the movement of the common driving shaft 20 to the lifter feet 16 ensues via identically fashioned cam disks 21 that are firmly connected to the driving shaft 20. Each cam disk 21 operates a lever 22 that, in turn, engages a lifter foot 16 and presses it against the floor. The lifter foot 16 is directly accepted in a guide bushing 23 or via a further guide bush (34 in FIGS. 5 and 6). The cam disks 21 are fashioned such that they enable a defined lift of, for example, 30 mm; the lifter feet 16 are no longer lowered given a further movement of the cam disks.

One of the lifter feet 16 is fashioned as a leveling foot 17 in order to be able to compensate a possible floor unevenness. It is guided with its shank 24 via a pin 25 in an oblong hole 26 in the guide bushing 34. Further, a spring element 27 that presses the leveling foot 17 against the floor is arranged in the guide bushing 34 in the form of a coil spring.

An immobilizing device 28 is provided in order to immobilize the leveling foot 17 in its final position, which is reached when the end of the cam surface of the cam disk 21 is reached so that the guide bushing 34 and with the leveling foot 17 are not further lowered. This immobilizing device 28 includes a second cam disk 29 that is also firmly arranged on the common driving shaft 20. This cam disk 29 has a cam surface which only comes to engage (act on) a guide pin 30 after the cam disk 21 has been rotated so as to complete its lifting effect. Then the cam disk 29 downwardly moves a guide pin 30 given a further rotation of the driving shaft 20. The guide pin 30 transfers, in turn, the force to a pressure pin 31. This pressure pin 31 is inserted into an opening 32 in the guide bushing 34. A brake lining 33 is situated in the opening 32, this brake lining 33 being pressed onto the die shank 24 by means of the pressure pin 31, causing the leveling foot 17 to be clamped in its position. The patient bed stands tilt-free as a result. After the immobilizing device 15 is released by pivoting the driving shaft 20 back by means of the operating element 35, the feet 16 move upwardly again and the patient bed is lowered on the guiding rollers 2 and can be moved again.

Although modifications and changes may be suggested by those skilled in the art, it is the intention of the inventors to embody within the patent warranted hereon all changes and modifications as reasonably and properly come within the scope of their contribution to the art.

We claim as our invention:

1. A urological patient bed comprising:
   a pedestal;
   a table top supported on said pedestal, said table top comprising a first plate section composed of X-ray transparent material, and a second plate section; and
   said first plate section and said second plate section respectively comprising separate plate modules and being detachably fastened at said table top, adjacent to each other, and being exchangeable in position with each other, to selectively reconfigure said table top to one of a plurality of different configurations.

2. A urological patient bed as claimed in claim 1 comprising at least one further plate section which is detachably fastenable to at least one of said first plate section and said second plate section.

3. A urological patient bed as claimed in claim 2 wherein said at least one further plate section is detachable from one of said first and second plate sections and is attachable to the other of said first and second plate sections.

4. A urological patient bed as claimed in claim 3 further comprising an insertion-type connection for detachably attaching said at least one further plate section to at least one of said first and second plate sections.

5. A urological patient bed as claimed in claim 4 wherein said insertion-type connection comprises an insertion-type latch connection.

6. A urological patient bed as claimed in claim 2 comprising at least two further plate sections having respectively different lengths.

7. A urological patient bed as claimed in claim 1 wherein said second plate section comprises a recess which is open toward one side of said second plate section, and a recess insert which is removably insertable into said recess to close said recess.

8. A urological patient bed as claimed in claim 7 wherein said second plate section has a width, and wherein said recess occupies at a quarter of said width.

9. A urological patient bed as claimed in claim 1 wherein said pedestal has a pedestal bottom, and further comprising a plurality of roller elements and support elements which are detachably mounted at said bottom of said pedestal, and said bottom of said pedestal comprising two mirror-symmetric sets of mounting locations for said roller elements and said support elements, said roller elements and support elements being detachably mounted at respective locations within one of said sets.

10. A urological patient bed as claimed in claim 9 wherein said roller elements comprise two fixed rollers and two guide rollers and wherein said support elements comprise a lifting mechanism and two lifter feet which are operated by said lifting mechanism, said fixed rollers being disposed at a first side of said bottom of said pedestal and said lifting feet being disposed at a second side, opposite to said first side, of said bottom of said pedestal, and said guide rollers being disposed between said fixed rollers and said lifting feet, said lifting mechanism being connected to said lifting feet to deploy said lifting feet to lift said bottom of said pedestal at said second end, so that said bottom of said pedestal rests on said fixed rollers and on said lifter feet.

11. A urological patient bed as claimed in claim 10 wherein one of said lifter feet comprises a spring-biased leveling foot.

12. A urological patient bed as claimed in claim 11 further comprising an immobilization device, selectively engageable with said leveling foot, for immobilizing said leveling foot at a position which levels said bottom of said pedestal.

13. A urological patient bed as claimed in claim 12 wherein said leveling foot comprises a shank and a guide bushing mounted in said bottom of said pedestal which receives said shank therein, said bushing having an opening in a side thereof, and wherein said immobilization device comprises a brake lining disposed in said bushing in registration with said opening, and a selectively activatable pressure pin extending through said opening in said bushing for, when activated, pushing said brake lining against said shank to immobilize said shank in said bushing.

14. A urological patient bed as claimed in claim 10 wherein said lifter mechanism comprises a common drive element connected to both of said lifter feet.

15. A urological patient bed as claimed in claim 14 wherein said common drive element comprises a drive shaft with two cam disks thereon, and wherein each of said lifter feet has a lever engageable therewith, operated by one of said cam disks, to deploy the respective lifter foot away from said bottom of said pedestal as said drive shaft and said cam disk are rotated.

16. A urological patient bed as claimed in claim 15 further comprising an immobilization device, selectively engageable with said leveling foot, for immobilizing said leveling foot at a position which levels said bottom of said pedestal, wherein said leveling foot comprises a shank and a guide bushing mounted in said bottom of said pedestal which receives said shank therein, said bushing having an opening in a side thereof, and wherein said immobilization device comprises a brake lining disposed in said bushing in registration with said opening, and a selectively activatable pressure pin extending through said opening in said bushing for, when activated, pushing said brake lining against said shank to immobilize said shank in said bushing.

17. A urological patient bed as claimed in claim 16 wherein said common drive element further comprises two further cam disks on said drive shaft, and wherein said immobilization device, for each of said lifter feet, further comprises a guide pin operated by said further cam disk after said first cam disk completes displacement of said lever, to activate said pressure pin to press against said brake lining.

\* \* \* \* \*